United States Patent
House

(10) Patent No.: US 6,811,754 B2
(45) Date of Patent: Nov. 2, 2004

(54) BIOLOGICAL SPECIMEN COLLECTION APPARATUS

(76) Inventor: Cherie G. House, 4419 Ringwood Rd., Nokesville, VA (US) 20181

( * ) Notice: Subject to any disclaimer, the term of this patent is extended or adjusted under 35 U.S.C. 154(b) by 287 days.

(21) Appl. No.: 09/912,829

(22) Filed: Jul. 25, 2001

(65) Prior Publication Data

US 2003/0021735 A1 Jan. 30, 2003

(51) Int. Cl.[7] ................................................ B01L 3/00
(52) U.S. Cl. .................. 422/102; 422/99; 422/104; 4/114.1; 4/144.1; 4/144.2; 4/144.3; 220/476; 220/480; 220/699; 220/700
(58) Field of Search ..................... 422/99, 102, 104; 206/438, 569; 220/400, 403, 476, 480, 604, 696, 699, 700; 4/114.1, 144.1, 144.2, 144.3

(56) References Cited

U.S. PATENT DOCUMENTS

| | | | | |
|---|---|---|---|---|
| 3,466,145 A | * | 9/1969 | Van Duyne | .......................... 4/1 |
| 3,571,817 A | * | 3/1971 | Gosnell | ........................... 4/110 |
| 3,625,654 A | * | 12/1971 | Van Duyne | .................. 23/253 |
| 4,137,573 A | * | 2/1979 | Kroeger | ....................... 4/144.1 |
| 4,203,169 A | * | 5/1980 | Dale | ........................... 4/144.1 |
| 4,244,920 A | * | 1/1981 | Manschot et al. | .......... 422/102 |
| 4,309,782 A | * | 1/1982 | Paulin | ............................ 4/661 |
| D267,342 S | | 12/1982 | Laible | |
| 5,060,317 A | * | 10/1991 | Bertelsen | ..................... 4/144.2 |
| 5,062,304 A | * | 11/1991 | Van Buskirk et al. | ........ 73/861 |
| 5,146,637 A | * | 9/1992 | Bressler et al. | ................. 4/445 |
| 5,422,076 A | * | 6/1995 | Jones | ......................... 422/102 |
| 5,487,393 A | | 1/1996 | Haswell et al. | |
| 5,558,840 A | | 9/1996 | Jones et al. | |
| D409,747 S | | 5/1999 | Aiken | |
| 6,013,230 A | | 1/2000 | Kuchar | |
| D425,983 S | | 5/2000 | Wilkinson et al. | |
| 6,151,972 A | * | 11/2000 | Venter et al. | ............ 73/863.41 |
| 6,212,698 B1 | * | 4/2001 | Stingley et al. | ................ 4/315 |
| 6,358,477 B1 | | 3/2002 | Webb et al. | |

OTHER PUBLICATIONS

Product Information for VOLLRATH Commode Specimen Collection Unit (12/99).

* cited by examiner

Primary Examiner—Jill Warden
Assistant Examiner—Dwayne K Handy
(74) Attorney, Agent, or Firm—Timothy R. Kroboth

(57) ABSTRACT

A versatile biological specimen collection apparatus is disclosed. Beneficially, the apparatus includes a receptacle for catching a biological specimen, and a support bracket for the receptacle, and the support bracket is adapted to be supported by a support structure such as a toilet bowl.

14 Claims, 2 Drawing Sheets

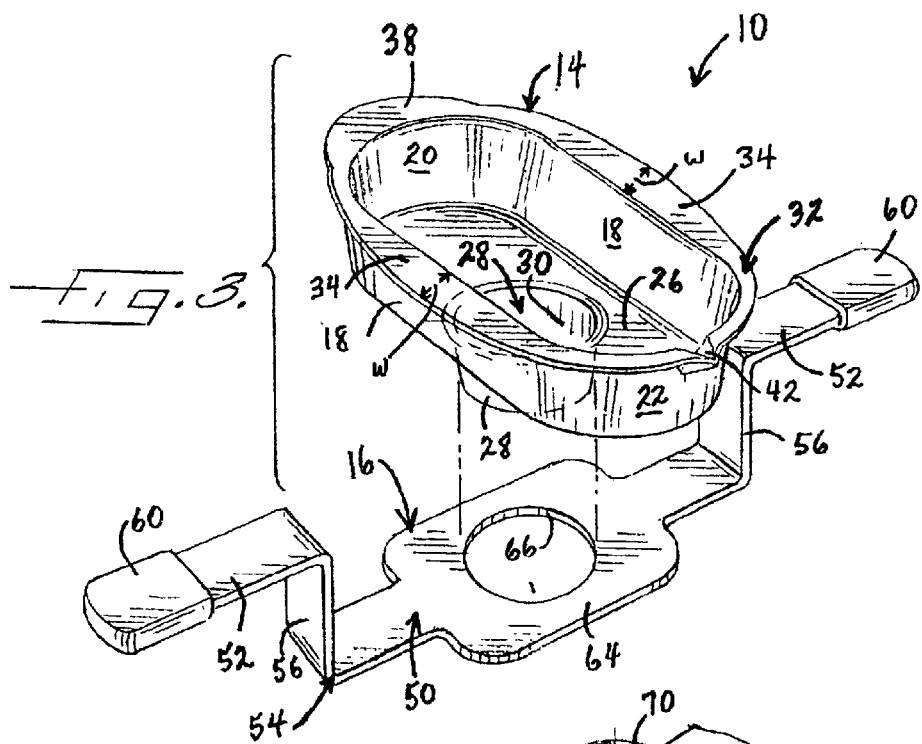
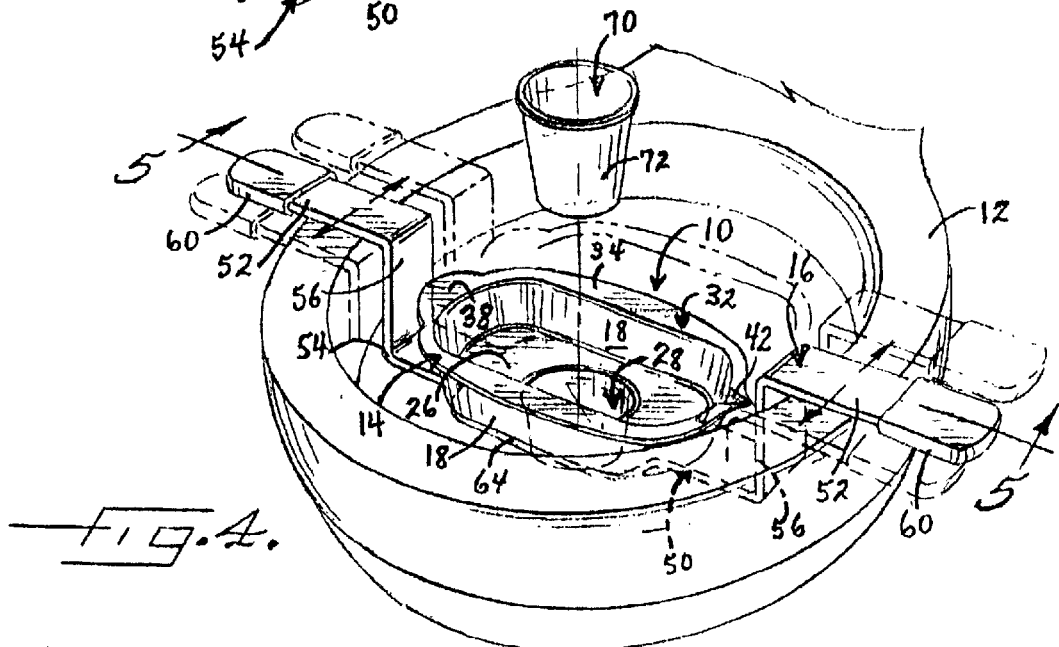
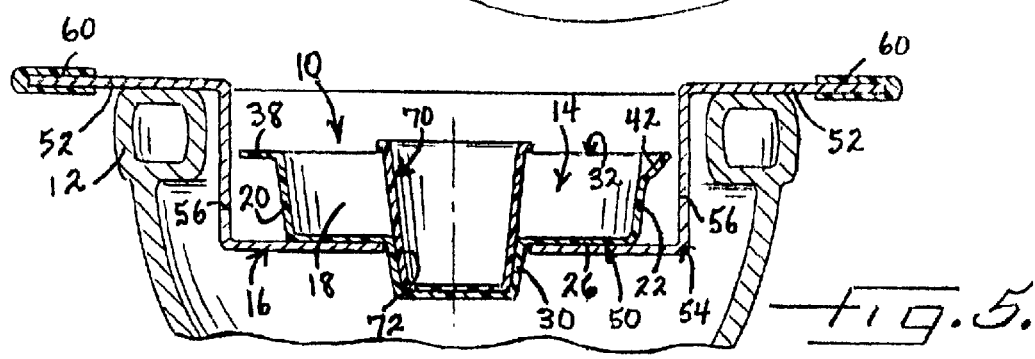

BIOLOGICAL SPECIMEN COLLECTION APPARATUS

FIELD OF THE INVENTION

This invention relates to a specimen collection apparatus for use with a support structure such as a toilet bowl.

BACKGROUND OF THE INVENTION

Giving biological specimens such as urine samples, can be particularly problematic for females, especially pregnant or obese females, the elderly and disabled, and children. Often the hand of the person giving the specimen or holding the specimen cup, may be inadvertently contacted by the specimen, or the person giving the specimen may have anxiety or be unable to relax. Furthermore, midstream samples are typically required when urine is to be cultured for possible infection; and in such case, a specimen collector is inserted into the path of the urine stream after urination is in progress. In the case of such individuals, collecting a midstream sample may be even more unpleasant or difficult.

Specimen cup holders are well known and are exemplified by U.S. Pat. Nos. 6,013,230 to Kuchar and U.S. Pat. No. 5,558,840 to Jones et al. However, these devices require that the holders be held by the person giving the specimen or another person. Elongated specimen collection devices are illustrated by U.S. Pat. No. 5,487,393 to Haswell et al and U.S. Design Pat. Nos. 409,747 to Aiken and U.S. Pat. No. 425,983 to Wilkinson et al.

Despite advances in the art of specimen collection apparatus, the foregoing problems with collecting biological specimens, continue to remain unsolved. There is therefore a significant need for an improved biological specimen collection apparatus.

SUMMARY OF THE INVENTION

In accordance with the present invention, there is provided a biological specimen collection apparatus for use with a support structure such as a toilet bowl. Beneficially, the apparatus includes a receptacle for catching a biological specimen, and a support bracket for the receptacle, wherein the support bracket includes an aperture and is adapted to be supported by the support structure, and the receptacle includes a boss that snugly fits, but is removably engageable from, the bracket aperture. Advantageously, the specimen may be given by a person seated on the support structure, and the receptacle is positioned vertically in space to avoid contact with the person but facilitate capture of the specimen.

A further advantageous aspect of the invention is that the receptacle may be an elongated receptacle, and the snugly fit, receptacle boss may be rotatable within the support bracket aperture for beneficial positioning of the receptacle. A yet further advantageous feature of the invention is that the support bracket may be adjustably mounted and include ends that extend sufficiently beyond the support structure for convenient positioning of the support bracket and hence of the receptacle by an individual seated on the support structure. A still further advantageous feature of the invention is that the receptacle boss may correspond to a generally cup-shaped cavity in a bottom wall of the receptacle, for receiving at least a lower portion of a specimen collection cup.

Additional advantages and beneficial features of the present invention are set forth in the drawing and detailed description, and in part will become apparent to those skilled in the art upon examination of the drawing and detailed description or may be learned by practice of the invention. In the drawing and detailed description, there is shown and essentially described only a preferred embodiment of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing which forms a part of the specification of the present invention.

FIG. 3 is an exploded perspective view of the urine collection apparatus of FIG. 1;

FIG. 4 is a view similar to FIG. 1 but with the toilet seat raised, a different orientation of the urine catch basin, and an optional sterile collection cup in exploded position, and which illustrates in phantom line forward/rearward adjustability of the support bracket; and FIG. 5 is a cross-sectional view taken substantially through line 5—5 of FIG. 4, with the collection cup in place in the urine catch basin.

DETAILED DESCRIPTION OF THE INVENTION

Figure 1:
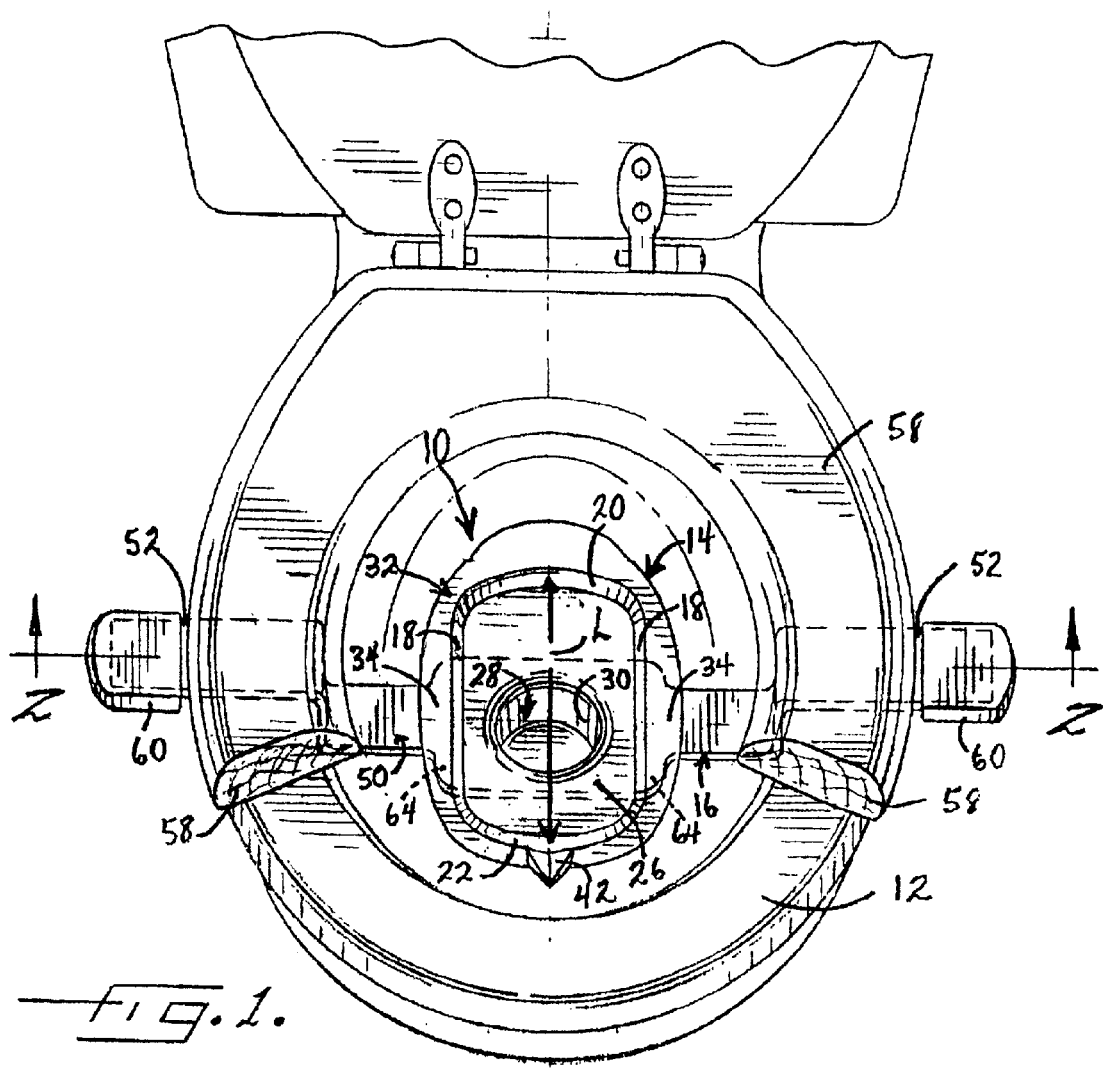
FIG. 1 is a top view of a preferred embodiment of a urine collection apparatus in accordance with the invention, supported by a toilet bowl and with the toilet seat down.

In accordance with the present invention, there is provided a biological specimen collection apparatus that is especially useful for collecting urine specimens from females, especially pregnant or obese females. The apparatus will advantageously reduce inadvertent specimen contact, assist the elderly, the disabled and children in giving specimens, and help a person giving a specimen to relax by allowing the person to be seated when giving the specimen.

Although the preferred embodiment depicted in the drawing and the detailed description are primarily directed to urine specimen collection, a biological specimen collection apparatus in accordance with the invention, may benefit collection of other specimens such as stools. As will be understood, terms such as "bottom", "below", "upper", "lower", "above", "horizontal", "vertical" and the like are relative, and have been particularly used with reference to the drawing to assist understanding.

With reference to the drawing, a urine collection apparatus 10 in accordance with the invention, is beneficially used in combination with a toilet bowl 12, or like structure that can support the urine collection apparatus and a seated person giving a specimen. Advantageously, the urine collection apparatus includes a receptacle or catch bowl 14 for catching a urine sample, and a bracket 16 for supporting and holding the catch receptacle in position, and for adjusting the catch receptacle position. As shown, bracket 16 is in turn supported by toilet bowl 12 or other suitable supporting structure.

Although receptacle 14 can be made of a material that could be sterilized for re-use, the receptacle is beneficially disposable, and for this reason, may be made of a plastic or other economically appropriate material. On the other hand, bracket 16 may be re-used, and in addition, because of the support function of the bracket, bracket 16 may conveniently be made of a durable and sterilizable material of suitable thickness and strength for providing the necessary support, such as stainless steel.

Receptacle 14 can have a variety of catch shapes. Although a generally circular catch shape can be used, the receptacle may advantageously have an elongated shape, for instance, a generally elliptical catch shape, or in particular with reference to FIGS. 1, 3 and 4, a generally rectangular catch shape having generally linear sides 18, but opposing ends 20, 22 that are curved or arcuate. An elongated catch shape beneficially provides for adjustability of the catch position without adjustment of the support bracket. More specifically, an elongated catch shape allows a catch position as shown in FIG. 1, in which the receptacle has a catch position further forward of the support bracket (an elongated dimension L of the receptacle being generally perpendicular to the support bracket), than when the elongated dimension is oriented generally parallel to the support bracket as shown in FIG. 4.

With continued reference particularly to FIGS. 1 and 3, receptacle 14 beneficially further includes a bottom wall 26 with a generally cup-shaped cavity 28 having a circumferential wall 30, and in addition, a circumferential upper rim 32 for strength against twisting or distortion of the receptacle, for instance, during removal from the support bracket. Referring particularly to FIG. 3, the circumferential upper rim advantageously is of varying width, and more specifically includes areas 34 of extended width w on receptacle sides 18 and an extended end area 38, to assist in handling the receptacle, whether or not containing a specimen. As best appreciated from FIGS. 1 and 3, the circumferential rim gives receptacle 14 a generally elliptical overall appearance.

Referring again particularly to FIG. 3, receptacle 14 beneficially further includes a pour spout 42 to assist in pouring a fluid specimen from the receptacle. Conveniently, the pour spout interrupts circumferential rim 32, and is positioned in receptacle end 22, opposite to extended rim area 38. Although receptacle 14 can vary in volumetric capacity, depth and other dimensions, the volumetric capacity should exceed the volume of a specimen desired for an analysis of interest. Beneficially, as will be appreciated, the receptacles will nest for storage or shipping, in one another.

Figure 2:
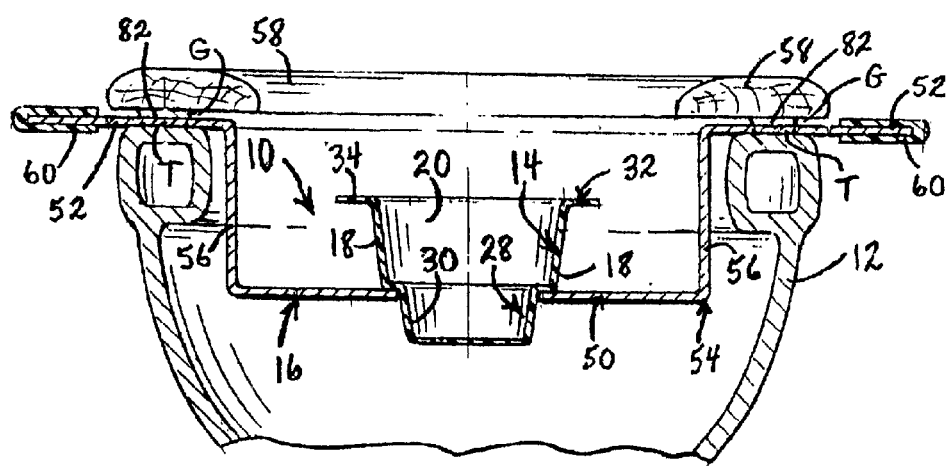
FIG. 2 is a cross-sectional view taken substantially along line 2—2 of FIG. 1.

As indicated, support bracket 16 not only will be of sufficient strength to support the weight of receptacle 14 and a specimen, but will have a lengthwise dimension sufficient for itself being supported by a support structure. Referring to FIGS. 2, 3 and 5, the bracket includes a receptacle support area 50 between bracket ends 52, and advantageously a generally U-shaped portion 54 of the bracket includes the receptacle support area. In this embodiment of the support bracket, bracket ends 52 are generally perpendicular to a pair of spaced apart legs 56 of the generally U-shaped portion. In any event, however, the receptacle support area will typically be generally horizontal when the bracket is in place on the support structure. Bracket ends 52 beneficially provide support contact with toilet bowl 12 and extend in length sufficiently beyond the toilet bowl to allow for convenient positioning of the support bracket by a person seated on a seat 58 for the toilet bowl, as further discussed later, and are covered by protective sheaths 60, which may be removably disposed of between uses, if desired.

Spaced apart legs 56 of generally U-shaped portion 54 of the bracket can have a variety of suitable heights, just as receptacle 14 can vary in depth. However, conveniently, the receptacle depth and height of bracket legs 56 are selected so that receptacle rim 32 is positioned, as best seen in FIGS. 2 and 5, below bracket ends 52, but suitably close to, for example, about one-half inch to four inches below, bracket ends 52. In any event, the receptacle should be positioned vertically in space to avoid contact with the body during specimen collection but facilitate capture of the specimen, and should be preferably within the toilet bowl space as illustrated in FIGS. 2 and 5. Likewise, the bracket configuration and positioning should be such as to avoid contact of the body of the person giving the specimen with the support bracket, except for any intended contact of hands with bracket ends 52 for adjustment of the receptacle position.

Typically and referring particularly to FIGS. 4 and 5, the bracket should be constructed so that the bracket legs are in a spaced apart position sufficient to accommodate positioning of the longest dimension of the receptacle generally parallel to the bracket. On the other hand, the bracket legs typically should be spaced close enough to permit appropriate forward positioning of the bracket with respect to the toilet bowl, it being recognized that a typical toilet bowl includes, as depicted in the drawing, a generally curved forward end.

Referring again to FIG. 3 in particular, receptacle support area 50 of the bracket advantageously includes a mid-portion 64 of enlarged width relative to the remaining portions of support area 50, for an appropriately sized aperture 66 that will beneficially allow a cup to be seated within a receptacle cavity. The enlarged bracket width provides not only for increased support of the receptacle, but also for an aperture shaped and sized to receive a receptacle boss that protrudes from bottom wall 26 and advantageously corresponds to cavity 28 in the receptacle bottom wall. Advantageously and with reference also to FIGS. 2 and 5, the bracket aperture and wall 30 of protrusion 28 are of mating shape and size so that there is a snug fit of the receptacle protrusion in the bracket aperture, i.e., a fit snug enough to restrain the receptacle from being inadvertently disengaged from the bracket, yet loose enough to be disengaged when appropriate.

As shown, aperture 66 is generally circular, and protuberance (and cavity) 28 is generally frustoconically shaped, and wall 30 thereof is a circumferential wall. Accordingly, boss 28 is beneficially rotatable within aperture 66, for any desired positioning of the receptacle after the receptacle has been mounted on the support bracket. However, other shapes of the receptacle protuberance and bracket aperture can be used, and the shape of the bracket aperture and cross-sectional wall shape need not be mating, but need only provide a snug fit in the bracket aperture. Thus, the term "boss" as used in this patent description, is not intended to limit the receptacle protuberance to a particular cross-section; for instance, the protuberance wall could have a square or hexagonal cross-section and the aperture could be correspondingly square or hexagonal.

Nevertheless and referring now to FIGS. 4 and 5, generally cup-shaped cavity 28 advantageously can be used to seat a cup 70 for catching a midstream urine sample. In such case, receptacle cavity 28 may receive at least a lower portion 72 of cup 70, and there beneficially will be a mating fit of at least the lower cup portion with cup-shaped cavity 28, and, as previously described, a mating fit of correspondingly projecting boss 28 with aperture 66. Advantageously, therefore, the circular aperture is of sufficient diameter to receive boss 28, which beneficially corresponds to cavity 28, which is of sufficient diameter to receive at least the lower portion of a conventional sterile cup, the fit being close enough to hold the cup securely in place for collection of a midstream sample in the cup.

It will be appreciated that lower portion 72 of the cup and the receptacle cavity do not need mating shapes; rather, the cavity need only receive lower portion 72 and provide a close enough fit. Furthermore, it will be appreciated that the receptacle could be provided with more than one cavity or boss, and that the support bracket could be provided with more than one boss-receiving aperture.

In use and referring initially to FIGS. 1 and 2, toilet seat 58 having spacer tabs 82 is lifted, support bracket 16 is placed on toilet bowl 12 so that bracket ends 52 are in support contact with the toilet bowl, and then the toilet seat is put down. Referring particularly to FIG. 2, the support bracket is movably mounted between toilet seat 58 and toilet bowl 12 because spacer tabs 82 provide a clearance gap G between the toilet seat and toilet bowl, the clearance gap being greater than a thickness T of bracket ends 52. Because bracket ends 52 extend sufficiently beyond the toilet bowl for convenient adjustment of the support bracket position when the toilet seat is down, the support bracket may advantageously be moved forward or rearward, as indicated by phantom line in FIG. 4, by a seated patient. Although FIG. 2 shows the support bracket positioned forward of the toilet seat spacer tabs, the support bracket may be located rearward of the spacer tabs, for example, when the spacer tabs are located near the forward end of a toilet seat.

The support bracket may be mounted on the toilet bowl with or without receptacle 14 in place. However, if not already in place, the receptacle is snugly fit to the support bracket by causing boss 28 to be seated in aperture 66, before a patient intending to give a specimen is seated on the toilet seat. FIGS. 1 and 2 indicate a position of an elongated receptacle that may be especially helpful for pediatric patients, in which the elongated dimension of the receptacle is positioned generally perpendicular to the support bracket, and the support bracket is positioned sufficiently close to the forward end of a toilet bowl so that the forward end of the elongated receptacle is beneath a lowered toilet seat.

If desired, the receptacle, though snugly fit to the support bracket, may be re-positioned by rotation of boss 28 in the generally circular bracket aperture. FIGS. 4 and 5 illustrate a second useful receptacle position, which may be obtained by re-positioning, or initially provided when boss 28 is seated in the bracket aperture. This position, in which the elongated dimension of an elongated receptacle is positioned generally parallel to the support bracket, may be especially helpful for a wide range of adults. Numerous other positions of an elongated receptacle vis-a-vis the support bracket exist and may be used as appropriate.

As mentioned, the support bracket is beneficially movably mounted on the support structure, and may advantageously be moved forward or rearward by a seated person grasping sheaths 60 covering bracket ends 52. Hence, a specimen collection apparatus in accordance with the invention, makes possible additional positioning of the receptacle after a person is seated in preparation for giving a specimen. Additional positioning may be especially useful for collecting a midstream urine specimen, for instance, in sterile cup 70. Thus, with urine collection apparatus 10 positioned to be out of the way of a urine stream until urination is in progress, the seated person may begin urinating and then by grasping the bracket ends may move the apparatus so that the cup 70 collects a midstream urine sample.

In any event, after a specimen is collected in receptacle 14, the receptacle will be removed from the support bracket by disengaging boss 28 from the support aperture by use of extended rim areas 34 and 38 of the receptacle. Thereafter, a portion of the specimen will typically be transferred into another container from receptacle 14 using pour spout 42, and that sample used for analysis, and the used receptacle discarded. A fresh receptacle may then be used with the support bracket for collecting another specimen. For home use, the bracket may be less durable and thus made of a very stiff plastic of suitable thickness and strength.

The present invention may be carried out with various modifications without departing from the spirit or essential attributes thereof, and accordingly, reference should be made to the appended claims, rather than to the foregoing specification as indicating the scope of the invention.

What is claimed is:

1. A biological specimen collection apparatus for use with a support structure, said apparatus comprising a receptacle having an elongated catch shape for catching a biological specimen and a support bracket for the receptacle, wherein the support bracket comprises a generally U-shaped portion provided with an aperture and is adapted to be supported by said support structure, and wherein the receptacle comprises a boss that snugly fits, but is removably engageable from, said aperture, and said receptacle boss is rotatable within paid aperture for adjustability of the catch position of the receptacle.

2. The apparatus of claim 1, further comprising a collection cup, wherein said receptacle boss corresponds to a generally cup-shaped cavity in a bottom wall of said receptacle, of an appropriate size for receiving at least a lower portion of said cup.

3. The apparatus of claim 1, where in said support bracket is non-planar and said generally U-shaped portion of said support bracket, when said support bracket is supported by said support structure, comprises a generally horizontal area provided with said aperture, and said receptacle is supported by said generally horizontal area and is positioned vertically in space to avoid body contact during specimen collection but facilitate capture of the specimen.

4. The apparatus of claim 1, wherein said elongated catch shape is a horizontally elongated catch shape when said receptacle is in supported engagement with said bracket.

5. The apparatus of claim 1, wherein said elongated catch shape is generally elliptical, and said generally U-shaped portion of said bracket comprises a pair of spaced apart legs that are spaced apart sufficiently to accommodate any position of said elongated receptacle relative to said bracket.

6. A biological specimen collection apparatus for use with a support structure, said apparatus comprising a receptacle for catching a biological specimen, a support bracket for the receptacle, and a collection cup, wherein the support bracket comprises a generally circular aperture and is adapted to be supported by said support structure and, wherein the receptacle comprises a generally frustoconically shapes boss that snugly fits, but is rotatable within and removably engageable from, said aperture,.

7. The apparatus of claim 6, wherein said support bracket is adjustably disposed with respect to said support structure when supported by said support structure, and comprises ends that extend beyond said support structure for positioning of said support bracket.

8. The apparatus of claim 6, wherein said support bracket is non-planar and said generally U-shaped portion of said support bracket, when said support bracket is supported by said support structure, comprises a generally horizontal area provided with said aperture, and said receptacle is supported by said generally horizontal area and is positioned vertically in space to avoid body contact during specimen collection but facilitate capture of the specimen.

9. The apparatus of claim 6, wherein said receptacle boss corresponds to a generally frustoconically shaped cavity in a bottom wall of said receptacle, of an appropriate diameter for receiving at least a lower portion of said cup, and said cup is a sterile cup.

10. The apparatus of claim 6, wherein said receptacle has an elongated catch shape, and said bracket comprises a generally U-shaped portion, and said generally U-shaped portion comprises a pair of spaced apart legs that are spaced apart sufficiently to accommodate any position of said elongated receptacle relative to said bracket.

11. A biological specimen collection apparatus for use with a support structure, said apparatus comprising a removably disposed receptacle for catching a biological specimen and a bracket for supporting the receptacle, wherein said receptacle has an elongated catch shape and a portion of the receptacle rotatably projects through said support bracket for adjustability of the catch position of the receptacle, and wherein said support bracket is supported by said support structure and is adapted to be adjustably disposed with respect to said support structure supported by said support structure, and said support bracket comprises oppositely extending ends that extend beyond said support structure for positioning of said support bracket.

12. The apparatus of claim 11, wherein said support structure is a toilet bowl, and a gap between said seat and support structure assists the support bracket adjustability.

13. A biological specimen collection apparatus for use with a support structure, said apparatus comprising a receptacle having an elongated catch share for catching a biological specimen, and a bracket for supporting the receptacle and adapted to be supported by said support structure, wherein the receptacle is rotatably mounted with respect to said support bracket for adjustability of the catch position of the receptacle, and a portion of the receptacle projects through, but is removably engageable from, said support bracket, and wherein said support bracket is further adapted to accommodate any position of the elongated, rotatably mounted receptacle relative to said bracket.

14. The apparatus of claim 13, further comprising a collection cup, wherein the projecting portion of the receptacle corresponds to a generally cup-shaped cavity in a bottom wall of the receptacle, and is dimensioned to provide a snug fit of the receptacle to said support bracket.

* * * * *